United States Patent
Fletter et al.

(10) Patent No.: US 11,458,283 B2
(45) Date of Patent: Oct. 4, 2022

(54) URINARY CATHETER ASSEMBLIES AND PACKAGING FOR SUCH ASSEMBLIES

(71) Applicant: Hollister incorporated, Libertyville, IL (US)

(72) Inventors: Paul C. Fletter, Mt. Prospect, IL (US); Robert A. Greynolds, Northbrook, IL (US); Denise Gamblin, Leeds (GB); Adam J. Foley, Swords (IE); Marine Veronique Germaine Richard, Carrieres sur Seine (FR)

(73) Assignee: Hollister Incorporated, Libertyville, IL (US)

( * ) Notice: Subject to any disclaimer, the term of this patent is extended or adjusted under 35 U.S.C. 154(b) by 131 days.

(21) Appl. No.: 16/763,137

(22) PCT Filed: Nov. 19, 2018

(86) PCT No.: PCT/US2018/061755
§ 371 (c)(1),
(2) Date: May 11, 2020

(87) PCT Pub. No.: WO2019/099975
PCT Pub. Date: May 23, 2019

(65) Prior Publication Data
US 2020/0398024 A1     Dec. 24, 2020

Related U.S. Application Data

(60) Provisional application No. 62/588,807, filed on Nov. 20, 2017.

(51) Int. Cl.
*A61M 25/00*   (2006.01)
*A61F 5/44*    (2006.01)
*A61F 5/443*   (2006.01)

(52) U.S. Cl.
CPC .......... *A61M 25/0017* (2013.01); *A61F 5/44* (2013.01); *A61F 5/443* (2013.01); *A61M 25/002* (2013.01);
(Continued)

(58) Field of Classification Search
CPC ............ A61M 25/0017; A61M 25/002; A61M 2202/0496; A61M 2210/1092;
(Continued)

(56) References Cited

U.S. PATENT DOCUMENTS 3,721,243 A    3/1973  Greth
3,742,953 A    7/1973  Lee
(Continued)

FOREIGN PATENT DOCUMENTS

EP    0185809 A1    7/1986
EP    2275058 A1    1/2011
(Continued)

OTHER PUBLICATIONS

International Search Report dated May 13, 2019 for International Application No. PCT/US2018/061755.

*Primary Examiner* — Tatyana Zalukaeva
*Assistant Examiner* — Hans Kaliher
(74) *Attorney, Agent, or Firm* — Cook Alex Ltd.

(57) ABSTRACT

A urinary catheter assembly (10) Includes a catheter tube (14), a connector (16), and a urine collection bag. The assembly further includes a package with a body receiving the catheter tube (18) and the urine collection bag (18) is in its compact configuration. The bag (18) may be variously configured, such as having a non-woven fabric backing portion and/or an outer adhesive or containing a superabsorbent polymer additive.

19 Claims, 7 Drawing Sheets

(52) U.S. Cl.
CPC ............... *A61M 2202/0496* (2013.01); *A61M 2210/1092* (2013.01)

(58) Field of Classification Search
CPC .......... A61M 2209/06; A61M 25/0054; A61M 2210/1089; A61M 1/60; A61F 5/44; A61F 5/4404; A61B 50/30; A45D 33/00; B65D 1/00; B65D 39/00
See application file for complete search history.

(56) References Cited

U.S. PATENT DOCUMENTS

| | | | |
|---|---|---|---|
| 3,894,540 | A | 7/1975 | Bonner |
| 4,029,099 | A | 6/1977 | Fifield |
| 4,057,062 | A | 11/1977 | Lavigne |
| 4,886,509 | A | 12/1989 | Mattsson |
| 4,889,532 | A | 12/1989 | Metz |
| 4,889,533 | A | 12/1989 | Beecher |
| 4,925,448 | A * | 5/1990 | Bazaral ............... A61M 25/002 206/364 |
| 5,010,599 | A | 4/1991 | Nilsson |
| 5,053,027 | A | 10/1991 | Manfredi |
| 5,662,630 | A * | 9/1997 | Raynie ..................... A61F 5/44 4/144.2 |
| 6,241,712 | B1 | 6/2001 | Steer |
| 6,416,500 | B1 | 7/2002 | Wada |
| 6,796,974 | B2 | 9/2004 | Palumbo |
| 6,887,230 | B2 | 5/2005 | Kubalak |
| 7,691,091 | B1 | 4/2010 | Baggett |
| 8,177,765 | B2 | 5/2012 | House |
| 8,241,262 | B2 | 8/2012 | Mahnensmith |
| 8,348,914 | B2 | 1/2013 | Zyburt |
| 8,388,587 | B1 | 3/2013 | Gmuer |
| 8,728,047 | B2 | 5/2014 | Ciok |
| 2002/0077609 | A1 | 6/2002 | Johnson |
| 2007/0244468 | A1 | 10/2007 | Kostandaras |
| 2008/0119803 | A1* | 5/2008 | Lund ................... A61M 27/008 604/327 |
| 2009/0036874 | A1* | 2/2009 | Horowitz .......... A61M 25/0017 604/544 |
| 2009/0088712 | A1 | 4/2009 | Ryder |
| 2011/0087181 | A1 | 4/2011 | Bidwell |
| 2012/0184944 | A1 | 7/2012 | Tomes |
| 2013/0226118 | A1 | 8/2013 | Enriquez |
| 2014/0094665 | A1 | 4/2014 | Ron |
| 2014/0194841 | A1 | 7/2014 | Matthiassen |
| 2014/0194842 | A1 | 7/2014 | Schertiger |
| 2014/0276500 | A1* | 9/2014 | Scott ..................... A61F 5/4404 604/343 |
| 2015/0018803 | A1 | 1/2015 | Tjassens |
| 2016/0067445 | A1* | 3/2016 | Murray ............. A61M 25/0043 604/544 |
| 2020/0214782 | A1* | 7/2020 | Wada .................. A61M 25/002 |

FOREIGN PATENT DOCUMENTS

| | | | |
|---|---|---|---|
| WO | 1999023978 A1 | 5/1999 | |
| WO | 2001062182 A2 | 2/2002 | |
| WO | WO-2003002179 A2 * | 1/2003 | ............ A61M 25/00 |
| WO | WO-2012134804 A1 * | 10/2012 | ............... B65B 7/02 |
| WO | 2013174382 A1 | 11/2013 | |
| WO | 2014142923 A1 | 9/2014 | |

\* cited by examiner

URINARY CATHETER ASSEMBLIES AND PACKAGING FOR SUCH ASSEMBLIES

CROSS-REFERENCE TO RELATED APPLICATION APPLICATIONS

This is the U.S. National Stage of International Application No. PCT/US2018/061755 filed Nov. 19, 2018 which claims the benefit of and priority to U.S. Provisional Patent Application Ser. No. 62/588,807, filed Nov. 20, 2017, the disclosures of all of which are hereby incorporated by reference in their entireties.

FIELD OF THE DISCLOSURE

The present disclosure is generally related to urinary catheters and packaging or containers for such catheters. More particularly, the present disclosure is directed to female urinary catheters having a pre-attached urine collection bag and compact packaging or containers for such catheters prior to use.

BACKGROUND

Intermittent catheterization is a good option for many people who suffer from various abnormalities of the urinary system. Those with such abnormalities often find it desirable to use individually-packaged, sterile catheter assemblies designed for a single use. These catheter assemblies typically include a catheter that is advanced into the urethra to drain urine therefrom. The urine flows through the catheter and into a waste bag, i.e., urine collection bag in fluid communication with the catheter. The catheter assembly is then disposed of, optionally with urine being emptied from the bag prior to disposal.

Users of intermittent catheters are often required to self-catheterize outside the privacy of the home, such as in public rooms. Thus, for these and other reasons, it is desirable that the intermittent catheters and urine collection bag be provided in discrete packaging that is also easy to open, compact, portable and allows for easy deployment of the catheter assembly.

Preferably, the package receives the other components of the catheter assembly in a compact configuration, for reduced storage space and, as noted above, discrete transport.

SUMMARY

There are several aspects of the present subject matter which may be embodied separately or together in the devices, systems, and/or methods described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a urinary catheter assembly includes a catheter tube, a connector, and a urine collection bag. The catheter tube includes proximal and distal ends, defines a flow path, and has one or more access eyelets at or adjacent to its proximal end. The connector includes a first surface associated with the catheter tube and a second surface associated with the urine collection bag, with the connector defining a flow path between the catheter tube and the urine collection bag. The connector is deformable between a compact configuration and an expanded configuration in which the catheter tube is spaced a greater distance from the urine collection bag than in the compact configuration. The assembly further includes a package with a body receiving the catheter tube and urine collection bag in a compact configuration.

In another aspect, disclosed herein is a package for storing and transporting a catheter assembly. The package includes a body for receiving a catheter tube and a pre-attached urine collection bag. The body includes a cavity for receiving a catheter tube and is configured to receive the urine collection bag in a compact condition. The package may optionally include a lid attached or attachable to the body.

In other aspects, the present disclosure is directed to urine collection bags that are pre-attached to the catheter tube(s) and received in the packages, or are used as stand-alone bags that may be attached at the time of use. Such urine collection bags include one or more of the following features: an outer surface wherein at least a portion of such surface is formed from a non-woven fabric material; an outer surface wherein at least a portion of such surface includes an adhesive; a rigid section configured to provide a folding surface; a super absorbent polymer additive configured to mix within the urine to increase the viscosity of the urine.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims. For example, embodied herein are: the complete catheter assembly which includes the catheter, the urine collection bag and the package for holding the catheter and the urine collection bag; the package itself; the urinary catheter and the urine collection bag, each of which may be part of the catheter assembly or separately provided.

Figures 1, 2, 3:
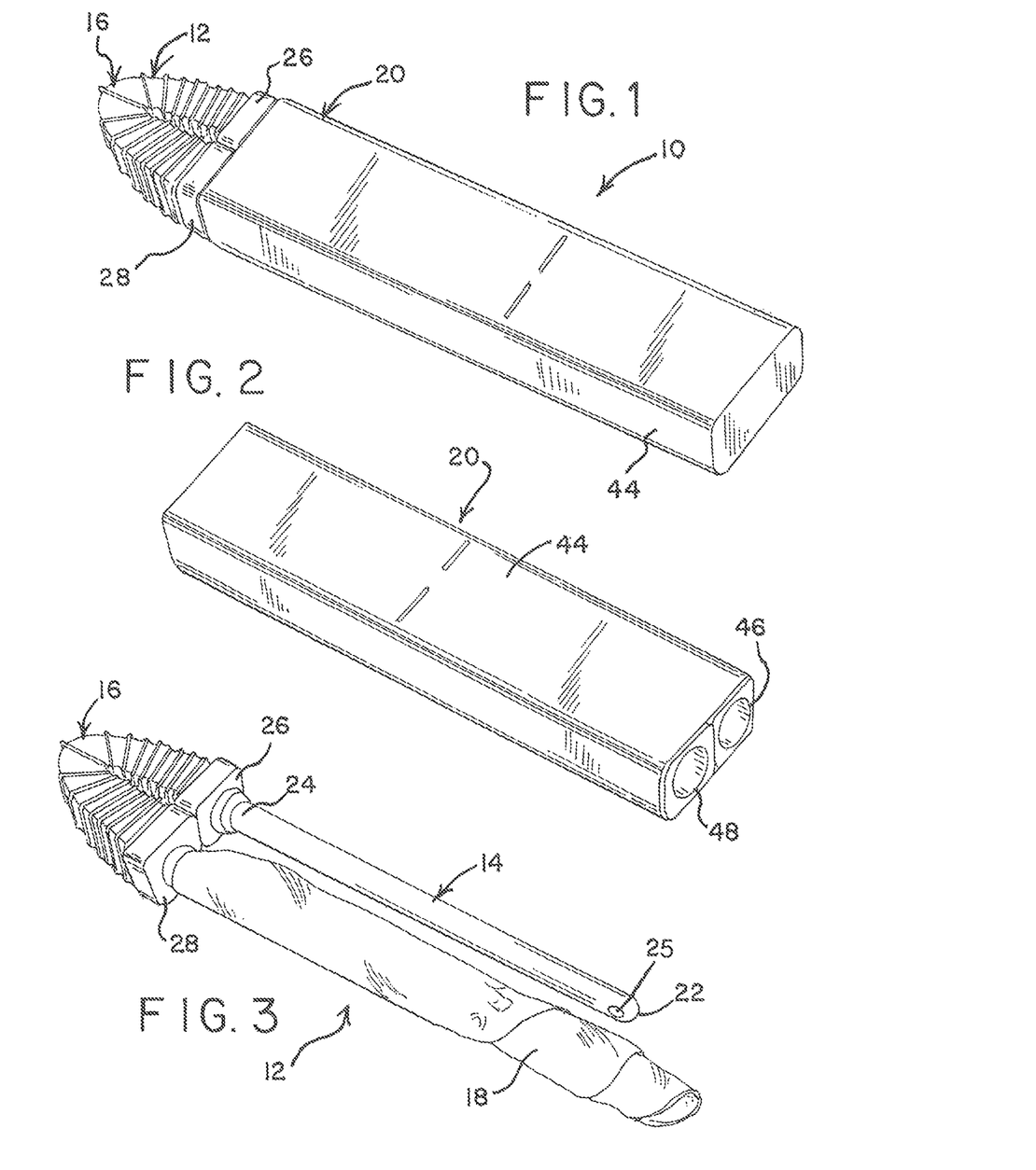
FIG. 1 is front perspective view of a urinary catheter assembly according to an aspect of the present disclosure.
FIG. 2 is a front perspective view of a package for the urinary catheter assembly of FIG. 1.
FIG. 3 is a front perspective view of a catheter of the urinary catheter assembly of FIG. 1.

FIGS. 1-3 show an embodiment of a urinary catheter assembly 10 according to an aspect of the present disclosure and individual components thereof. The urinary catheter assembly 10 includes a catheter 12 (FIG. 3), which includes a catheter tube 14, a connector 16, and a urine collection bag 18. The catheter tube 14 and urine collection bag 18 are received by a package 20 of the urinary catheter assembly 10 (FIG. 1) prior to use to ensure that the catheter tube 14 remains sterile as well as for purposes of lubricating or maintaining the lubricating of catheter tube 14. The connector 16 and the urine collection bag 18 are not advanced into the urethra during use of the catheter 12, so they may be at least partially positioned outside of the package 20 prior to use, as will be described in greater detail herein.

The catheter tube 14, which may be provided according to conventional design, is configured for insertion into the urethra of (typically) a female patient and extends from a proximal end 22 to a distal end 24. The proximal end 22 is configured as a closed tip, with one or more access eyelets 25 positioned at or adjacent to the proximal end 22 to allow urine to drain from the bladder and into the interior of the catheter tube 14.

The connector 16 defines a flow path between the catheter tube 14 and the urine collection bag 18. A first surface 26 of the connector 16 is associated with the distal end 24 of the catheter tube 14, while a second surface 28 of the connector 16 is associated with the urine collection bag 18. In the embodiment of FIG. 3, the first and second surfaces 26 and 28 of the connector 16 are opposing ends of the connector 16, but it is also within the scope of the present disclosure for one of the first and second surfaces to be a sidewall of the connector, as will be described in greater detail herein.

Figures 4, 5, 6:
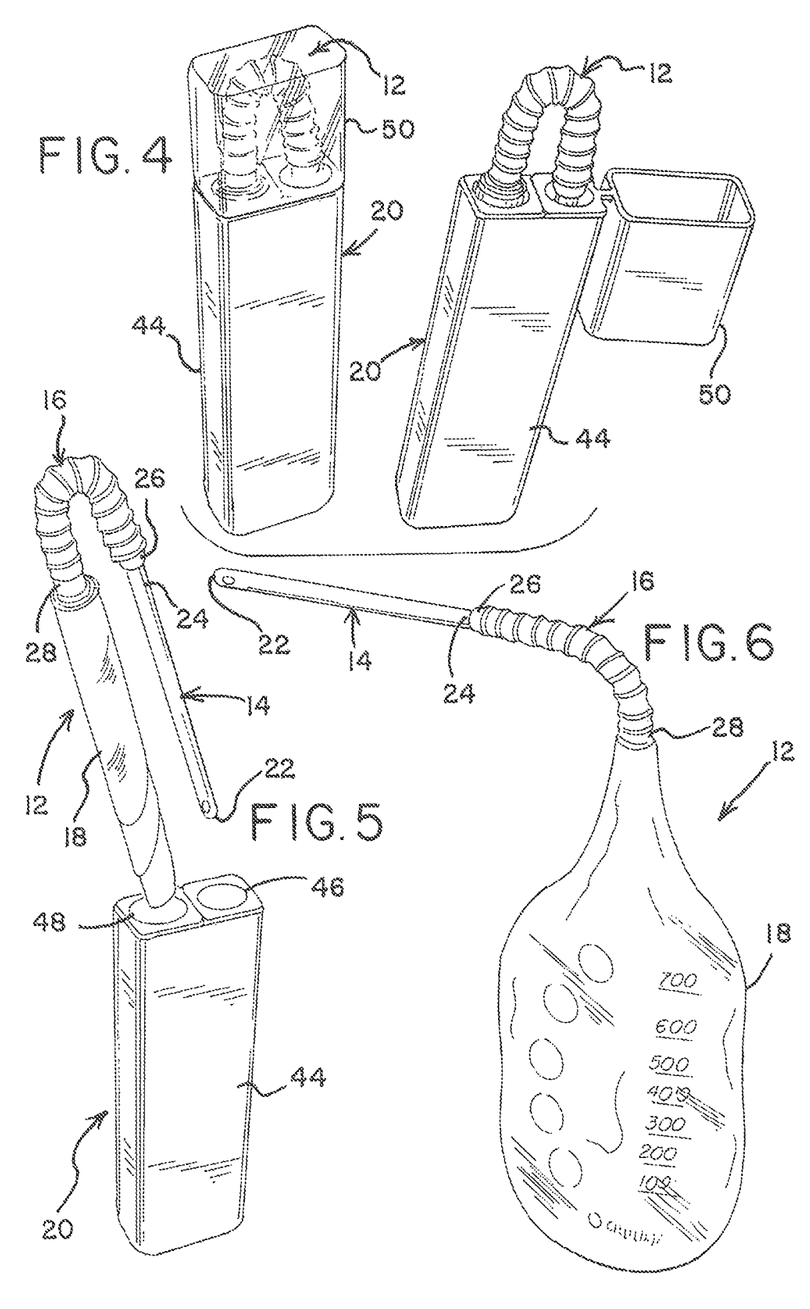
FIG. 4 includes front perspective views of a variation of the urinary catheter assembly of FIG. 1, with and without a cover enclosing a catheter of the urinary catheter assembly.
FIG. 5 is a front perspective view of the urinary catheter assembly of FIG. 1 or 4, with the catheter removed from a package of the urinary catheter assembly.
FIG. 6 is a front perspective view of the catheter of FIG. 5.

The connector 16 is movable or deformable between a compact configuration (FIGS. 1 and 3) and an expanded configuration (FIG. 6). In the compact configuration, the catheter tube 14 and the urine collection bag 18 are positioned relatively close together (e.g., in a side-by-side arrangement, as in FIGS. 3 and 5) for storage of at least the catheter tube 14 within the container 20, with the catheter tube 14 and the urine collection bag 18 being spaced a greater distance apart in the expanded configuration for use by a patient. The connector 16 may be variously configured without departing from the scope of the present disclosure. In the illustrated embodiment, the connector 16 is provided according to the disclosure of International Publication WO 2018/075464, which is hereby incorporated herein by reference.

For example, the illustrated connector 16 may be provided as a flexible, smooth plastic tubing or a flexible, pleated member that is extendable along a central axis of the connector 16, while also capable of being bent or deformed relative to its central axis to facilitate insertion and manipulation of the catheter tube 14 during self-catheterization. The connector 16 may be made of any resilient material that allows for movement in multiple (preferably, three) dimensions, such as extension/compression along its central axis, bending relative to its central axis, and twisting about its central axis. Polyvinyl chloride is a suitable material for use in forming the connector 16, but other materials may be used without departing from the scope of the present disclosure. The connector 16 may allow the catheter tube 14 to assume an angle or orientation with respect to the urine collection bag 18 that is advantageous to the patient, but not possible (or not possible without kinking) in the absence of the connector 16, as in FIG. 6.

As the connector 16 is not advanced into the urethra during catheterization, it may have a larger diameter than the catheter tube 14. A larger diameter may be advantageous for ensuring proper flow of urine from the catheter tube 14 into the urine collection bag 18 and for preventing over-insertion of the catheter 12 into the urethra. The connector 16 may, thus, be handled by the patient during self-catheterization to advance the catheter tube 14 into the urethra, in which case the pleats of the connector 16 may provide improved gripping and handling.

The urine collection bag 18 may be provided according to conventional design, being formed of a flexible, deformable material that allows the urine collection bag 18 to be moved between a compact or stored, non-deployed configuration or condition (FIGS. 3 and 5) and an expanded or deployed configuration or condition (FIG. 6). The primary function of the urine collection bag 18 is to retain urine drained from the bladder, but it may be variously configured to provide added functionality. For example, the urine collection bag 18 may include an opening or handle for improved handling. The urine collection bag 18 may alternatively or additionally include a frangible section or removable drain tap or valve that may be opened or exposed (such as by peeling a sticker 30, as in FIG. 19) to allow the urine collection bag 18 to be selectively opened for emptying urine into a toilet or other waste receptacle. In another embodiment, the urine collection bag 18 may be detachable from the connector 16 to drain urine from the urine collection bag 18.

As will be described in more detail below, catheter assembly of the type disclosed herein are carried and stored prior to use in a discrete package. The package includes a body that receives at least the catheter tube within an interior cavity or compartment. The body of the package may also be configured for receiving or otherwise accommodating the urine collection bag in a compact, non-deployed (e.g., rolled-up) condition either within a cavity in the body, or adjacent to the body of the package which may be configured to receive the collection container (in the above-described compact, undeployed condition) at the outside of the package body. The body may have one or more cavities to accommodate both the catheter and the urine collection bag. The package may further include a lid that cooperates with body of the package to enclose the catheter tube, at least a portion of the connector and optionally, the urine collection bag.

Turning now to the package 20 of FIGS. 1 and 2, it includes a body 44 that may be formed of a relatively rigid material (e.g., a plastic material). The body 44 defines generally parallel first and second cavities 46 and 48 (FIG. 2). The catheter tube 14 and the urine collection bag 18 are positioned side-by-side when the connector 16 is in its compact configuration (FIG. 3), such that the first cavity 46 receives at least a portion of (but more preferably the entire) catheter tube 14 and the second cavity 48 receives at least a portion of (but more preferably the entire) urine collection bag 18 (FIG. 1) prior to use of the catheter 12. Depending on the relative sizes of the urine collection bag 18 in its stored configuration and the catheter tube 14; the first and second cavities 46 and 48 may be differently configured, such as one having a greater diameter and/or depth than the other. The first cavity 46 may be filled with a hydrating fluid or media to maintain the catheter tube 14 in a properly lubricated state during storage.

The connector 16 remains outside of the container body 44, where it may be gripped by a patient to withdraw and deploy the catheter tube 14 and the urine collection bag 18 from the container 20 for use in one motion. In the embodiment of FIG. 1, the first and second ends 26 and 28 of the connector 16 are configured to seal the cavities 46 and 48 (respectively) of the container body 44, such that a separate cover is not required to surround the connector 16 for providing sterile storage of the catheter tube 14 and urine collection bag 18. A frangible seal or adhesive or a friction or interference fit between the connector 16 and the body 44 of package 20 may ensure that the catheter tube 14 and the urine collection bag 18 remain sterile during storage.

In an alternative embodiment, which is shown in FIG. 4, the package 20 may be provided with a cover or lid 50, which cooperates with body 44 to sterilely enclose the connector 16 when the lid 50 is in a closed configuration (as in the left half of FIG. 4). In one embodiment, the lid 50 is pivotally connected to the body 44, such that the lid 50 may be pivoted away from its closed configuration to an open configuration (as in the right half of FIG. 4) to break the sterile connection and allow access to the catheter 12. Alternatively, the cover 50 may be completely detachable from the container body 44 to allow access to the catheter 12 (as in FIG. 5).

Regardless of the particular configuration of the container 20, following use, the catheter tube 14 may be returned to the first cavity 46, with the emptied urine collection bag 18 being optionally wrapped around body 44 for disposal. It is also possible for the patient to return the urine collection bag 18 to its stored configuration (FIGS. 3 and 5) and place it back into the second cavity 48 of the container body 44 for more compact disposal or for storage if a waste receptacle is not immediately available. In yet another embodiment, the urine collection bag 18 may be detached from the connector 16 and separately disposed of.

Figures 7, 8, 9:
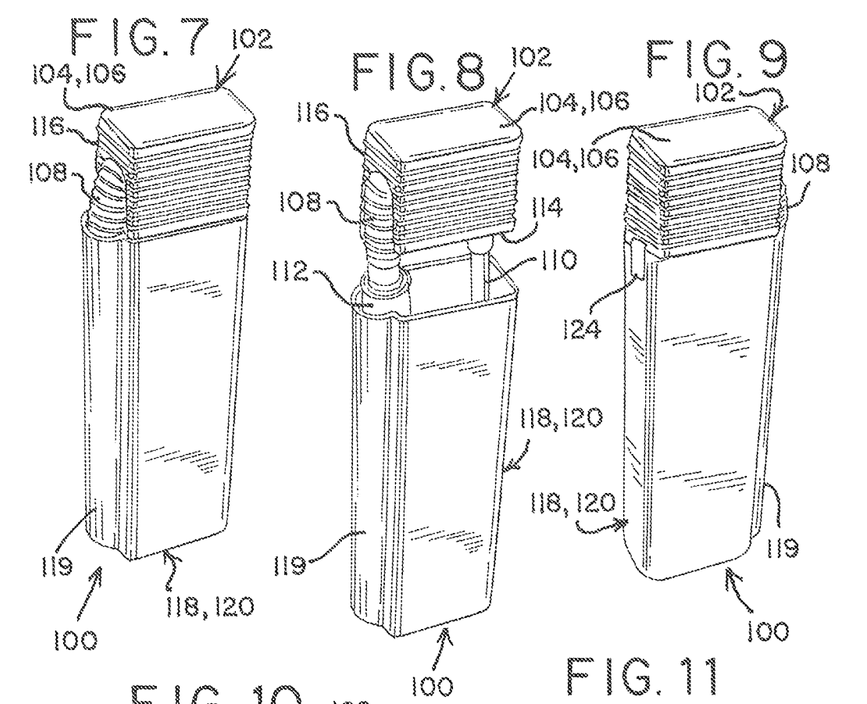
FIG. 7 is a front perspective view of another embodiment of a urinary catheter assembly according to an aspect of the present disclosure.
FIG. 8 is a front perspective view of the urinary catheter assembly of FIG. 7, with a catheter of the urinary catheter assembly partially removed from a package of the urinary catheter assembly.
FIG. 9 is a rear perspective view of the urinary catheter assembly of FIG. 7.
Figure 11:
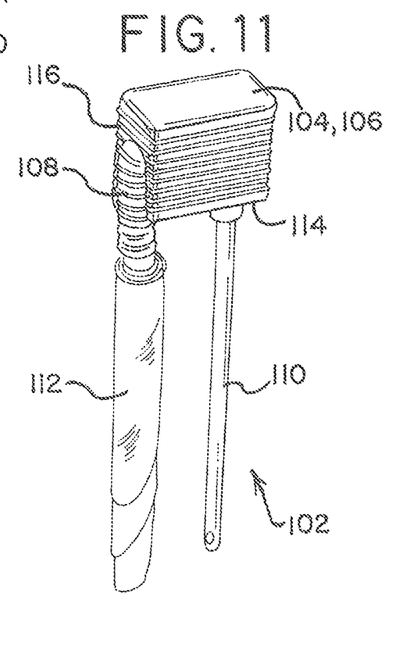
FIG. 11 is a front perspective view of a catheter of the urinary catheter assembly of FIG. 10.
Figures 12, 13:
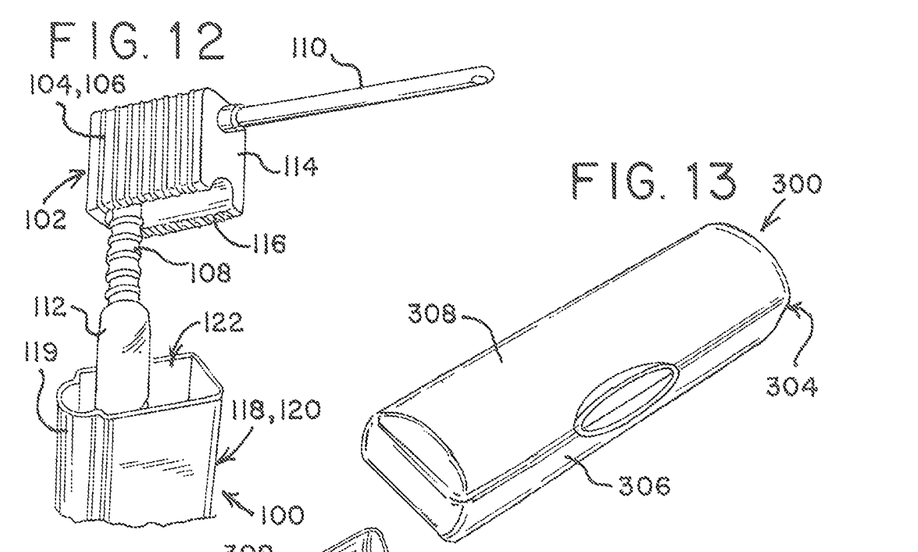
FIG. 12 is a front perspective view of the urinary catheter assembly of FIG. 7, with the catheter more fully removed from the package than in FIG. 8.
FIG. 13 is a front perspective view of another embodiment of a urinary catheter assembly according to an aspect of the present disclosure.

FIGS. 7-9 illustrate another embodiment of a urinary catheter assembly 100 according to the present disclosure. The catheter 102 of FIGS. 7-9 (which is also incorporated into the urinary catheter assembly 200 of FIG. 10, which will be described in greater detail herein) is shown in FIGS. 11 and 12 and includes a connector 104 that is differently configured from the connector 16 of the catheter 12 of FIGS. 1-6. The connector 104 of FIGS. 7-12 includes a body 106 that is optionally, but not necessarily, as deformable or flexible as the connector 16 of FIGS. 1-6. The connector body 106 need not be particularly deformable because it is provided with a port 108 that is pivotally or otherwise adjustably connected to the connector body 106 to allow for a high degree of reconfiguration between a compact configuration (FIGS. 7-11) and an expanded configuration (FIG. 12). For example, FIG. 12 shows the port 108 pivoted approximately 90° from its initial position, with the catheter tube 110 and urine collection bag 112 positioned side-by-side in the compact configuration, and spaced apart and oriented substantially perpendicularly in the expanded configuration. It should be understood that the illustrated compact and expanded configurations are merely exemplary and that the port 108 may be pivoted more than 90° from its initial position.

As in the embodiment of FIGS. 1-6, the first surface 114 of the connector 104 (which is associated with the catheter tube 110) is an end of the connector body 106. However, the second surface 116 is a sidewall of the connector body 106, rather than an opposing end of the connector body 106, as in FIGS. 1-6. It should be understood, though, that an adjustable port is not limited to incorporation into a sidewall of a connector body, but may instead be incorporated into an end of the connector body. Additionally, while the illustrated port 108 is associated with the urine collection bag 112, it should be understood that an adjustable port may instead (or additionally) be associated with the catheter tube 110.

The package 118 of FIGS. 7-9 includes a body 120 that may be formed of a relatively rigid material (e.g., a plastic material), defining a single cavity 122 (FIG. 12) receiving at least a portion (but preferably the entirety) of both the catheter tube 110 and the urine collection bag 112, which are positioned side-by-side when the connector 104 is in its compact configuration prior to use of the urinary catheter assembly 100. As shown in FIGS. 7-9, body 120 may be configured to include an outwardly extending wall portion 119 to provide an area within cavity 122 that accommodates urine collection bag 112 in its rolled-up, compact configuration. The cavity 122 may be filled with a hydrating fluid or media to maintain the catheter tube 110 in a properly lubricated state during storage.

The connector 104 remains outside of body 120 of package 118, where it may be gripped by a patient to withdraw and deploy the catheter tube 110 and the urine collection bag 112 from package 118 for use. The connector body 106 is preferably configured to seal the cavity 122 of the container body 120, such that a separate cover is not required to surround the connector 104 for providing sterile storage of the catheter tube 110 and urine collection bag 112. A frangible seal or adhesive or a friction or interference fit between the connector 104 and the container body 120 may ensure that the catheter tube 110 and the urine collection bag 112 remain sterile during storage. As can be seen in FIG. 9, the connector 104 may be secured to package 118 by a piece of tape 124 or the like, which must be peeled off or otherwise removed before the catheter 102 can be removed from the container 118. The tape 124, thus, may serve as a tamper-evident seal.

Figure 10:
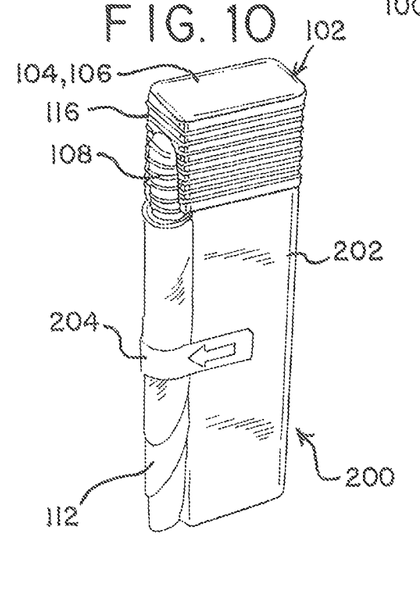
FIG. 10 is a front perspective view of a variation of the urinary catheter assembly of FIG. 7.

In an alternative embodiment, which is shown in FIG. 10, the package body 202 is smaller than in the embodiment of FIGS. 7-9, defining a single cavity receiving only the catheter tube 110, while the urine collection bag 112 is positioned outside of the container body 202. The urine collection bag 112 remains outside of the body during use, so it is not necessary for it to remain in a sterile condition, particularly when the connector 104 is present to space the urine collection bag 112 from the catheter tube 110, ensuring that the urine collection bag 112 is positioned away from the urethra during use. In the illustrated embodiment, the urine collection bag 112 is positioned directly adjacent to an outer, preferably flat, surface of the container body 202 (to minimize the size of the urinary catheter assembly 200), with a piece of tape or a strap 204 securing the urine collection bag 112 in place against the container body 202. The embodiment of FIG. 10 may be preferred to the embodiment of FIGS. 7-9 by some patients because the urine collection bag 112 is kept out of contact with a hydrating fluid or media that may be present in the cavity, thus providing a urine collection bag 112 with an outer surface that is completely dry during use.

Regardless of the particular configuration of the package body 120, 202, following use, the catheter tube 110 may be returned to the single cavity, with the emptied urine collection bag 112 being optionally wrapped around the container body 120, 202 for disposal or separated from the connector 104 for separate disposal. It is also possible for the patient to return the urine collection bag 112 to its stored configuration and place it back into the cavity 122 of the container body 120 in the embodiment of FIGS. 7-9 for more compact disposal or for storage if a waste receptacle is not immediately available.

Figures 14, 15:
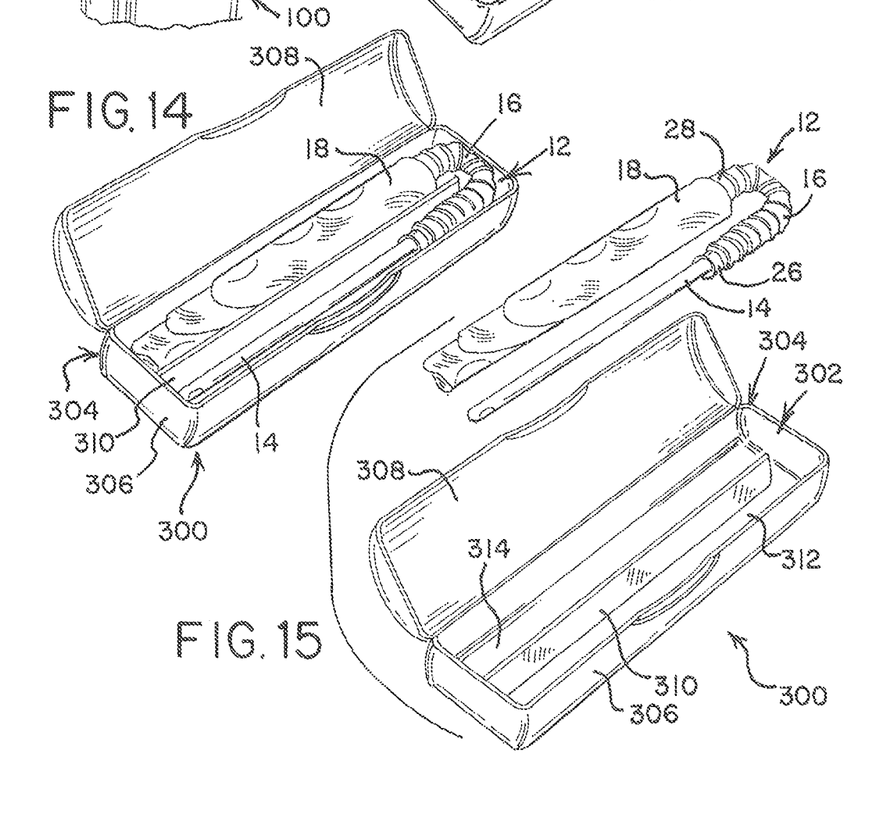
FIG. 14 is a front perspective view of the urinary catheter assembly of FIG. 13, with a lid of a package of the urinary catheter assembly in an open configuration.
FIG. 15 is a front perspective view of the urinary catheter assembly of FIG. 13, with a catheter of the urinary catheter assembly removed from the package.

FIGS. 13-15 illustrate another embodiment of a urinary catheter assembly 300 according to an aspect of the present disclosure. The urinary catheter assembly 300 is shown with a catheter 12 as in the embodiments of FIGS. 1-6, but it is also within the scope of the present disclosure for the catheter to be provided as in the embodiments of FIGS. 7-12 or differently configured. Regardless of the particular configuration of the catheter, it is completely received within a cavity 302 defined by an associated package 304. Package 304 includes a body 306 that may be formed of a relatively rigid material (e.g., a plastic material), with a lid 308 connected (e.g., pivotally connected) to the body 306 and movable between a closed configuration for sterile storage (FIG. 13) and an open configuration for removal of the catheter 12 (FIGS. 14 and 15). Due to the configuration of body 306, it may be placed onto a horizontal surface to provide a workspace while the patient makes preparations for self-catheterization, with the lid 308 in either its open or closed configuration.

The cavity 302 may include a rib or divider 310 separating the cavity 302 into first and second sections 312 and 314 (FIG. 15), with the catheter tube 14 received by the first section 312 and the urine collection bag 18 received by the second section 314. The connector 16 may be partially positioned in each section 312, 314 of the cavity 302, with the first surface 26 of the connector 16 positioned within the first section 312 with the catheter tube 14 and the second surface 28 of the connector 16 positioned within the second section 314 with the urine collection bag 18. In an alternative embodiment, the connector may be fully positioned within the first cavity, with an elongated urine collection bag extending from the first section 312 to the second section 314.

Following use (and after emptying the urine collection bag 18), the catheter 12 may be returned to the cavity 302, with the lid 308 being returned to its closed configuration for disposal. Alternatively, the emptied urine collection bag 18 may instead be wrapped around the container 304 for disposal.

Figures 16, 17, 18, 19:
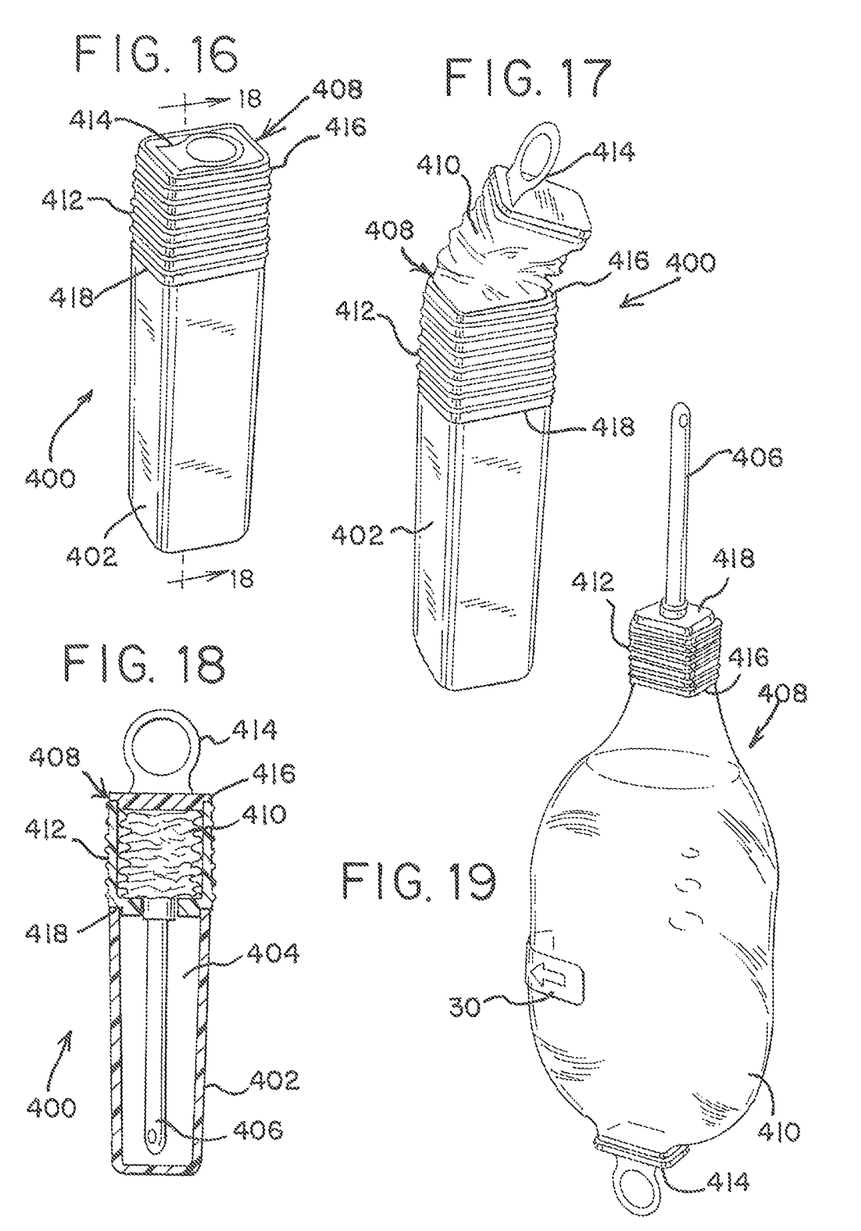
FIG. 16 is a front perspective view of another embodiment of a urinary catheter assembly according to an aspect of the present disclosure.
FIG. 17 is a front perspective view of the urinary catheter assembly of FIG. 16, with a urine collection bag of the urinary catheter assembly partially removed from a connector of the urinary catheter assembly.
FIG. 18 is a cross-sectional view of the urinary catheter assembly of FIG. 16, taken through the line 18-18 of FIG. 16.
FIG. 19 is a front perspective view of a catheter of the urinary catheter assembly of FIG. 16.

FIGS. 16-18 illustrate another embodiment of a urinary catheter assembly 400 according to an aspect of the present disclosure. As in the embodiment of FIG. 10, the urine catheter assembly 400 of FIGS. 16-18 includes a container 402 with a body defining an elongated cavity 404 receiving only the catheter tube 406 of a catheter 408, while a urine collection bag 410 remains outside of the package 402. Cavity 404 may include hydrating fluid or other element for making and/or maintaining the lubricity of tube 406. However, the catheter 408 is differently configured, with a connector 412 that receives the urine collection bag 410 in a stored configuration, as best shown in FIG. 18. The urine collection bag 410 may include a pull tab 414 or the like associated with a second surface 416 of the connector 412 to enclose the remainder of the urine collection bag 410 within the connector 412. The pull tab 414 (which may lay flat during storage, as in FIG. 16) may be grasped by a patient and moved away from the connector 412 to withdraw the urine collection bag 410 from inside the connector 412 and move it to a deployed configuration for use.

As for the package 402, it is detachably connected to a first surface 418 of the connector 412 (which may be an end of the connector 412 opposite the second surface 416) to sterilely enclose the catheter tube 406. In use, the urine collection bag 410 may be removed from the connector 412 while the catheter tube 406 remains within the container 402 (FIG. 17). When the patient is ready for self-catheterization, the container 402 may be detached from the connector 412 to break the sterile seal and expose the catheter tube 406 (FIG. 19), with the catheter tube 406 subsequently being advanced into the urethra.

After use, package 402 may be reconnected to the connector 412 to enclose the catheter tube 406. The emptied urine collection bag 410 may be wrapped around the package 402 and/or the connector 412 or separated from the connector 412 for disposal.

Figure 20:
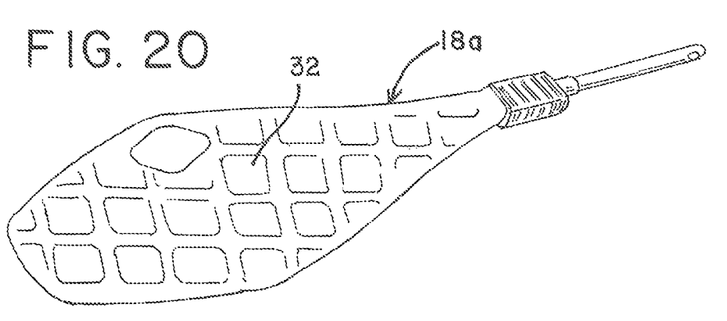
FIG. 20 is a front perspective view of a catheter having a urine collection bag that may be incorporated into a urinary catheter assembly according to the present disclosure.

FIGS. 20-25 illustrate other features that may be incorporated into urine collection bags according to the present disclosure. FIG. 20 shows an embodiment of a urine collection bag 18a in which at least a portion thereof (which may be a portion of an outer surface of the urine collection bag 18a) is formed of a non-woven fabric material 32. For example, in one embodiment, the urine collection bag 18a is formed of two sheets of material joined at their perimeters, in which case the non-woven fabric material 32 may overlay an entire one of the sheets. It may be particularly advantageous for the non-woven fabric material 32 to be positioned at a location that may come into contact with the body (e.g., the leg) of a patient during use. The non-woven fabric material 32 may have improved softness and noise reduction compared to the typical flexible plastic material that is used to form a conventional urine collection bag. Additionally, the non-woven fabric material 32, which is opaque, may be wrapped around the remainder of the catheter to camouflage the catheter in a waste receptacle.

Figure 21:
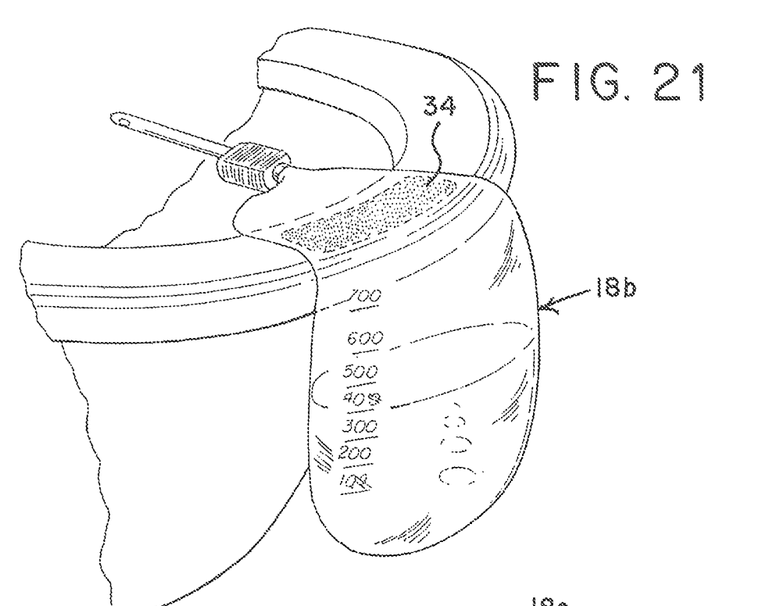
FIG. 21 is a front perspective view of another catheter having a urine collection bag that may be incorporated into a urinary catheter assembly according to the present disclosure.

FIG. 21 illustrates another feature that may be incorporated into the urine collection bags of urinary catheter assemblies according to the present disclosure. In FIG. 21, the urine collection bag 18*b* includes an adhesive 34 that may be used to secure the urine collection bag 18*b* to a surface of a toilet during use. The adhesive 34 may be covered by a backing layer prior to use, with the backing layer being removed to expose the adhesive 34 for securing the urine collection bag 18*b* to the toilet. The adhesive 34 may comprise a pressure-sensitive adhesive, which forms a temporary bond with a surface of the toilet when pressed against the toilet, but is readily removable from the toilet by the patient following use.

Figure 22:
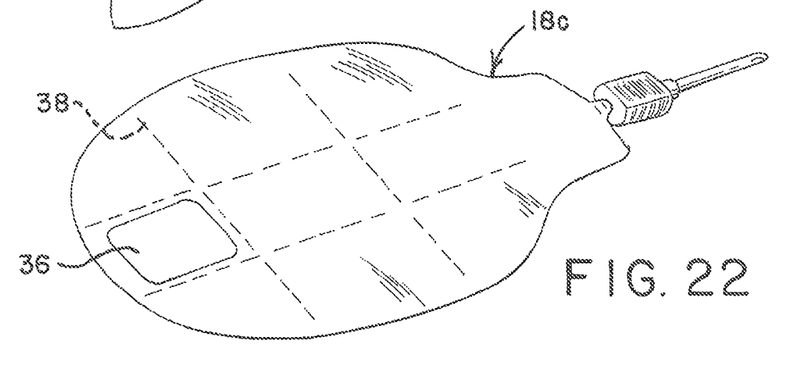
FIG. 22 is a front perspective view of yet another catheter having a urine collection bag that may be incorporated into a urinary catheter assembly according to the present disclosure.

FIG. 22 illustrates yet another feature that may be incorporated into the urine collection bags of urinary catheter assemblies according to the present disclosure. In FIG. 22, the urine collection bag 18*c* includes a relatively rigid section or card 36 configured to provide a folding surface for moving the urine collection bag 18*c* from its illustrated deployed configuration to a compact or folded configuration. FIG. 22 shows fold lines 38 where the urine collection bag 18*c* would be folded against the relatively rigid section 36 for a more compact folded configuration, for easing replacement of the associated catheter into a container or for reducing the space taken up by the catheter in a waste receptacle.

Figure 23:
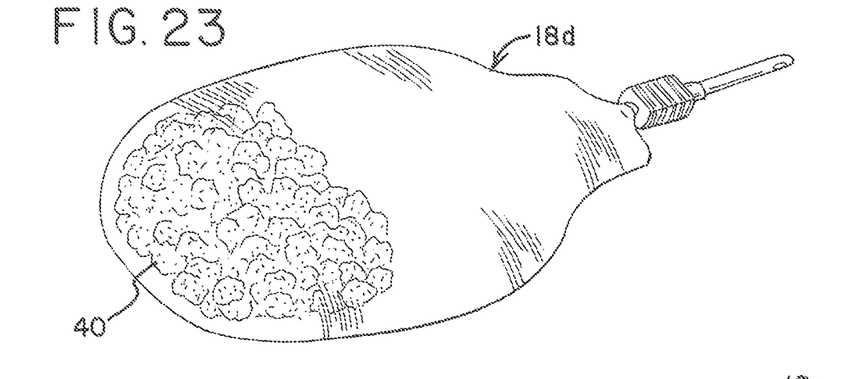
FIG. 23 is a front perspective view of a catheter having a urine collection bag filled with a superabsorbent polymer additive, as may be incorporated into a urinary catheter assembly according to the present disclosure.

FIG. 23 illustrates an embodiment in which the urine collection bag 18*d* is partially filled with a superabsorbent polymer additive 40 configured to mix with urine to increase the viscosity of the urine in the urine collection bag 18*d*. The additive 40 may be provided as a powder or may be contained within a burst pack. When the additive 40 mixes with urine, a gel is formed, which reduces sloshing, spilling, and leakage of the urine when emptying the urine from the urine collection bag 18*d*.

Figures 24, 25:
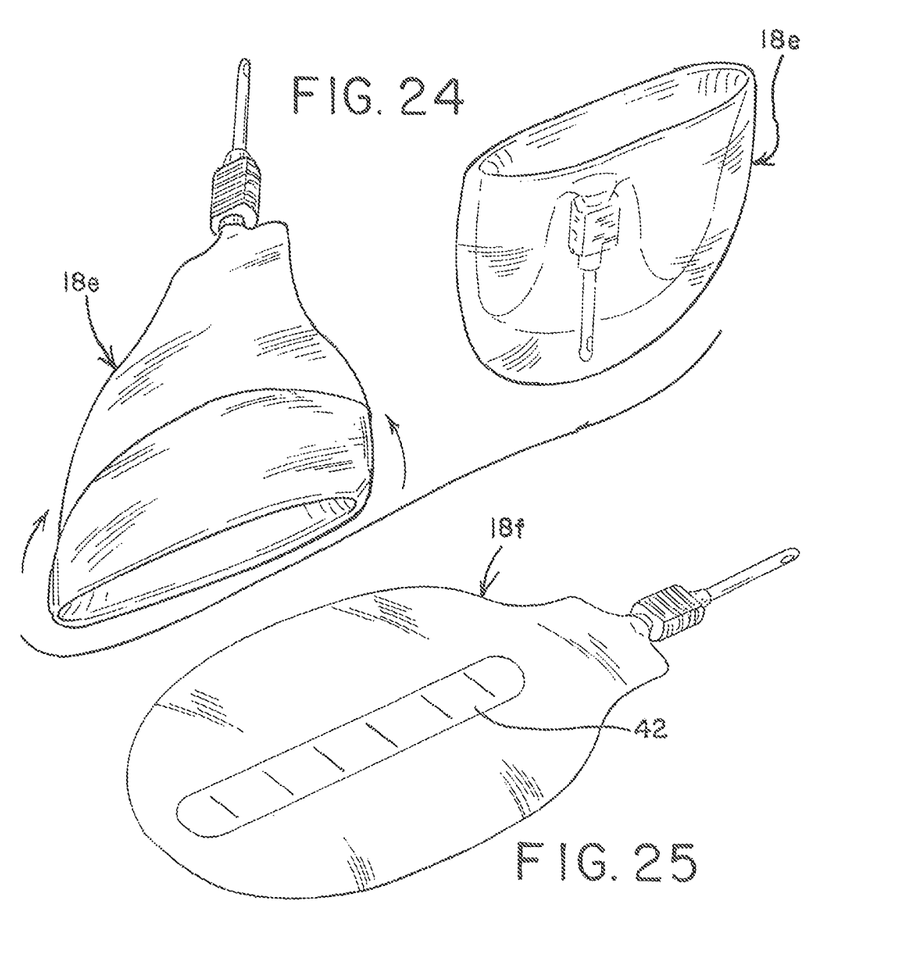
FIG. 24 includes front perspective views of a catheter having an invertible urine collection bag that may be incorporated into a urinary catheter assembly according to the present disclosure.
FIG. 25 is a front perspective view of a catheter having a urine collection bag with a viewing window, as may be incorporated into a urinary catheter assembly according to the present disclosure.

FIG. 24 illustrates an embodiment of a urine collection bag 18*e* that may be inverted (after emptying it of urine) to receive at least a portion of the associated catheter tube and connector for disposal. More preferably, the urine collection bag 18*e* is sized and configured to be inverted to receive the entire catheter tube, as in the illustrated embodiment.

FIG. 25 illustrates an embodiment of a urine collection bag 18*f* in which the majority of the urine collection bag 18*f* is formed of an opaque material, with a viewing window 42 allowing observation of the interior of the urine collection bag 18*f*. The primarily opaque urine collection bag 18*f* may allow for more discrete disposal (e.g., being wrapped around the other components of the associated urinary catheter assembly following use), while the viewing window 42 allows a patient to monitor urine color and (if the viewing window 42 is provided with gradations, as in FIG. 25) the volume of urine. The features of the urine collection bags of FIGS. 20-25 may be employed separately or in any combination.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A urinary catheter assembly comprising:
   a catheter tube including a proximal end and a distal end, said catheter tube defining a flow path and including one or more access eyelets at or adjacent to said proximal end;
   a connector including first and second surfaces, with the distal end of the catheter tube associated with the first surface of the connector;
   a urine collection bag associated with the second surface of the connector, wherein
     the connector defines a flow path between said catheter tube and said urine collection bag, and
     the connector is deformable between a compact configuration and an expanded configuration in which the catheter tube is spaced a greater distance from the urine collection bag than in the compact configuration; and
   a package including a body defining a cavity configured to receive rcceiving the catheter tube and said urine collection bag, with the connector and said urine collection bag in the compact configuration, and wherein at least one of the first or second surfaces of the connector is configured to seal the cavity.

2. The urinary catheter assembly of claim 1, wherein the catheter tube and the urine collection bag are positioned side-by-side when the connector is in the compact configuration.

3. The urinary catheter assembly of claim 1, wherein at least a portion of the connector is positioned outside of the body of the package.

4. The urinary catheter assembly of claim 3, further comprising a cover movable between a closed configuration and an open configuration, wherein
   the cover cooperates with the body of the package to sterilely enclose the connector when the cover is in the closed configuration, and
   the connector is accessible when the cover is in the open configuration.

5. The urinary catheter assembly of claim 4, wherein the cover is pivotally connected to the body of the package.

6. The urinary catheter assembly of claim 1, wherein
   the body of the package defines generally parallel first and second cavities,
   the first cavity receives the catheter tube, and
   the second cavity receives the urine collection bag.

7. The urinary catheter assembly of claim 1, wherein the catheter tube, the connector, and the urine collection bag are received within the body of the package.

8. The urinary catheter assembly of claim 7, wherein
   the body of the package defines a single cavity including a rib separating the single cavity into first and second sections,
   the first section receives the catheter tube,
   the second section receives the urine collection bag,
   the first surface of the connector is received by the first section, and
   the second surface of the connector is received by the second section.

9. The urinary catheter assembly of claim 8, further comprising a lid movable between a closed configuration and an open configuration, wherein
the lid cooperates with the body of the package to sterilely enclose the catheter tube, the urine collection bag, and the connector when the lid is in the closed configuration, and
the catheter tube, the urine collection bag, and the connector are accessible when the lid is in the open configuration.

10. A urinary catheter assembly comprising:
a catheter tube including a proximal end and a distal end, said catheter tube defining a flow path and including one or more access eyelets at or adjacent to said proximal end;
a connector including first and second surfaces, with the distal end of the catheter tube associated with the first surface of the connector;
a urine collection bag associated with the second surface of the connector, wherein
the urine collection bag is movable between a stored configuration where the urine collection bag is received within the connector and a deployed configuration where the urine collection bag is positioned outside of the connector,
the connector defines a flow path between said catheter tube and said urine collection bag, and
the connector is deformable between a compact configuration and an expanded configuration in which the catheter tube is spaced a greater distance from the urine collection bag than in the compact configuration; and
a package including a body receiving the catheter tube and said urine collection bag, with the connector in the compact configuration and said urine collection bag in the stored configuration, wherein the package is detachably connected to the first surface of the connector.

11. The urinary catheter assembly of claim 10, wherein the urine collection bag includes a pull tab configured to be moved away from the connector to move the urine collection bag from the stored configuration to the deployed configuration.

12. The urinary catheter assembly of claim 1, wherein a portion of an outer surface of the urine collection bag includes an adhesive.

13. The urinary catheter assembly of claim 1, wherein the urine collection bag includes a relatively rigid section configured to provide a folding surface for moving the urine collection bag from a deployed configuration to a folded configuration.

14. The urinary catheter assembly of claim 1, wherein the urine collection bag includes a superabsorbent polymer additive configured to mix with urine in the urine collection bag to increase the viscosity of the urine in the urine collection bag.

15. The urinary catheter assembly of claim 1, wherein the urine collection bag is invertible to receive at least a portion of the catheter tube and the connector for disposal.

16. The urinary catheter assembly of claim 1, wherein a majority of the urine collection bag is formed of an opaque material, and the urine collection bag includes a viewing window configured to allow observation of an interior of the urine collection bag.

17. A urinary catheter assembly comprising:
a catheter tube including a proximal end and a distal end, said catheter tube defining a flow path and including one or more access eyelets at or adjacent to said proximal end;
a connector including first and second surfaces, with the distal end of the catheter tube associated with the first surface of the connector;
a urine collection bag associated with the second surface of the connector, wherein
the connector defines a flow path between said catheter tube and said urine collection bag, and
the connector is deformable between a compact configuration and an expanded configuration in which the catheter tube is spaced a greater distance from the urine collection bag than in the compact configuration; and
a package including a body defining at least one cavity, wherein the catheter tube and the urine collection bag are positioned side-by-side when the connector is in the compact configuration and wherein the catheter tube is stored within the at least one cavity and said urine collection bag is stored outside of the at least one cavity.

18. The urinary catheter assembly of claim 17, wherein the urine collection bag is located within the package body.

19. The urinary catheter assembly of claim 17, wherein the urine collection bag is located outside of the package body.

* * * * *